United States Patent [19]
Taylor et al.

[11] Patent Number: 6,066,639
[45] Date of Patent: May 23, 2000

[54] 5,6,7,8-TETRAHYDROPYRIDO[2,3-D] PYRIMIDINES

[75] Inventors: Edward C. Taylor, Princeton, N.J.; Chuan Shih, Carmel, Ind.; Koo Lee, Taejon, Rep. of Korea; Lynn S. Gossett, Indianapolis, Ind.

[73] Assignees: The Trustees of Princeton University, Princeton, N.J.; Eli Lilly and Company, Indianapolis, Ind.

[21] Appl. No.: 09/171,772

[22] PCT Filed: Sep. 17, 1996

[86] PCT No.: PCT/US96/14822

§ 371 Date: Feb. 26, 1999

§ 102(e) Date: Feb. 26, 1999

[87] PCT Pub. No.: WO97/41115

PCT Pub. Date: Nov. 6, 1997

Related U.S. Application Data

[60] Provisional application No. 60/021,174, May 1, 1996.

[51] Int. Cl.$^7$ ............................ A61K 31/519; C07D 401/14
[52] U.S. Cl. .............................................. 514/258; 544/279
[58] Field of Search ............................... 544/279; 514/258

[56] References Cited

U.S. PATENT DOCUMENTS

| | | | |
|---|---|---|---|
| 5,473,071 | 12/1995 | Taylor et al. | 548/279 |
| 5,508,281 | 4/1996 | Gangjee | 514/258 |
| 5,516,776 | 5/1996 | Barnett et al. | 514/258 |
| 5,536,724 | 7/1996 | DeGraw et al. | 514/258 |
| 5,786,358 | 7/1998 | Shih et al. | 514/258 |

FOREIGN PATENT DOCUMENTS

97/49075 12/1997 WIPO.

*Primary Examiner*—Mukund J. Shah
*Assistant Examiner*—V Balasubramanian
*Attorney, Agent, or Firm*—Mathews, Collins, Shepherd & Gould, P.A.

[57] ABSTRACT

Glutamic acid derivatives in which the amino group is substituted with a 2-amino-5,6,7,8-tetrahydropyrido[2,3-d]pyrimidin-6-ylalkyl-Z-carbonyl group, in which Z is a divalent, five-membered, nitrogen-containing heterocyclic ring system optionally containing a sulfur or nitrogen atom as a second hetero ring member, are antineoplastic agents. A typical embodiment is N-{3-[2-(2-amino-4-hydroxy-5,6,7,8-tetrahydropyrido[2,3-d]pyrimidin-6-yl)ethyl]-pyrazol-5-ylcarbonyl}-L-glutamic acid.

15 Claims, No Drawings

5,6,7,8-TETRAHYDROPYRIDO[2,3-D] PYRIMIDINES

This application is a 371 of PCT/US96/14822 filed Sep. 17, 1996, which claims the benefit of U.S. Provisional Application Ser. No. 60/021,174 filed May 1, 1996.

This invention relates to 5,6,7,8-tetrahydropyrido[2,3-d] pyrimidines of the formula:

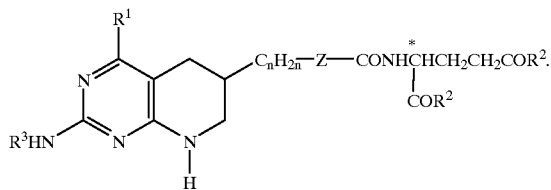

I in which $R^1$ is hydroxy or amino;

$R^2$ is hydroxy or a carboxylic acid protecting group;

$R^3$ is hydrogen or an amino protecting group;

Z is a divalent, five-membered, nitrogen-containing heterocyclic ring system optionally containing a sulfur or nitrogen atom as a second hetero ring member, the valence bonds originating from nonadjacent carbon atoms of the heterocyclic ring; and n has a value of 2 or 3.

The present invention also pertains to the pharmaceutically acceptable salts of the 5,6,7,8-tetrahydropyrido[2,3-d] pyrimidines of Formula I.

In addition, the invention pertains to a method of inhibiting neoplastic growth in a mammal in which the growth is dependent on folic acid, or a metabolic derivative of folic acid (such as $N^5,N^{10}$-methylenetetrahydrofolate), as a substrate. The method comprises administering, in a single or multiple dose regimen, an effective amount of a compound according to Formula I to a mammal in need of such therapy.

Finally, the invention pertains to pharmaceutical compositions for inhibiting such neoplastic growth in a mammal through inhibition of folate enzymes which comprises a compound according to Formula I in combination with a pharmaceutically acceptable carrier.

The compounds of Formula I are named herein as derivatives of the pyrido[2,3-d]-pyrimidine fused ring system which is numbered as follows:

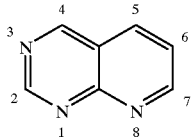

It will be appreciated that the pyrido[2,3-d]pyrimidines of Formula I are the tautomeric equivalent of the corresponding 3-H-4-oxo or 3-H-4-imino structures. For simplicity's sake, the compounds are depicted herein as 4-hydroxy and 4-amino compounds, it being understood the corresponding and tautomeric keto and imino structures, respectively, are fully equivalent; e.g.:

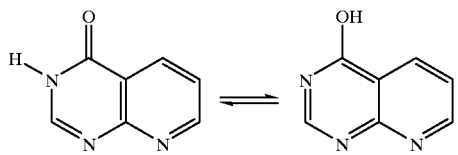

The compounds of Formula I can be employed in the form of the free dicarboxylic acid, in which case both $R^2$ groups are hydroxyl. Alternatively, the compounds often can be employed in the form of a pharmaceutically acceptable salt, in which case the hydrogen atom when $R^2$ is hydroxy is replaced by a pharmaceutically acceptable cation. Such salt forms, including hydrates thereof, are often crystalline and advantageous for forming solutions or formulating pharmaceutical compositions. Pharmaceutically acceptable salts with bases include those formed from the alkali metals, alkaline earth metals, non-toxic metals, ammonium, and mono-, di- and trisubstituted amines, such as for example the sodium, potassium, lithium, calcium, magnesium, aluminum, zinc, ammonium, trimethylammonium, triethanolammonium, pyridinium, and substituted pyridinium salts. The mono and disodium salts, particularly the disodium salt, are advantageous.

In addition to the center of chirality about the carbon atom on the glutamic acid designated *, a second chiral center is present in the 6-position of the 5,6,7,8-tetrahydropyrido[2, 3-d]pyrimidine ring system. Both the therapeutically active diastereomeric mixtures and the individual diastereomers are included in the scope of this invention. When both individual diastereomers are formed, they can be separated mechanically as by chromatography or chemically by forming salts with a chiral acid, such as the individual enantiomers of 10-camphorsulfonic acid, camphoric acid, alphabromocamphoric acid, tartaric acid, diacetyltartaric acid, malic acid, pyrrolidone-5-carboxylic acid, and the like, and then freeing one or both of the individual diastereomeric bases, optionally repeating the process, so as obtain either or both substantially free of the other; i.e., in a form having an optical purity of >95%.

The protecting groups designated by $R^2$ and $R^3$ utilized herein denote groups which generally are not found in the final therapeutic compounds but which are intentionally introduced at some stage of the synthesis in order to protect groups which otherwise might be altered in the course of chemical manipulations. Such protecting groups are removed at a later stage of the synthesis and compounds bearing such protecting groups thus are of importance primarily as chemical intermediates (although some derivatives also exhibit biological activity). Accordingly the precise structure of the protecting group is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol. 15/I, Georg Thieme Verlag, Stuttgart 1974, the disclosures of which are incorporated herein by reference.

With respect to $R^2$, a carboxy group can be protected as an ester which is selectively removable under sufficiently mild conditions not to disrupt the desired structure of the molecule, especially a lower alkyl ester of 1 to 12 carbon atoms such as methyl or ethyl and particularly one which is branched at the 1- or α position such as t-butyl; and such lower alkyl ester substituted in the 1- or 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichloroethyl, 2-bromoethyl, and 2-iodoethoxycarbonyl; (iv) one or two phenyl groups each of which can be unsubstituted or mono-, di- or tri-substituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)methyl; or (v) aroyl, such as phenacyl. A carboxy group also can be protected in the form of an organic silyl group such as trimethylsilylethyl or tri-lower alkylsilyl, as for example tri-methylsilyloxycarbonyl.

With respect to $R^3$, an amino group can be protected as an amide utilizing an acyl group which is selectively removable under mild conditions, especially formyl, a lower alkanoyl group which is branched in 1- or α position to the carbonyl group, particularly tertiary alkanoyl such as pivaloyl, or a lower alkanoyl group which is substituted in the position α to the carbonyl group, as for example trifluoroacetyl.

In the compounds of Formula I, Z is a divalent, five-membered, nitrogen-containing heterocyclic ring system. Optionally the ring may containing a sulfur or nitrogen atom as a second hetero ring member. The depicted valence bonds of Z originate from nonadjacent carbon atoms of the ring. Z thus can be, for example, pyrrolediyl, imidazolediyl, pyrazolediyl, thiazolediyl, or isothiazolediyl. It will be appreciated that when the divalent heterocyclic group comprised by Z is asymmetric, as for example pyrrole-2,4-diyl (as contrasted with the symmetrical pyrrole-2,5-diyl), the single group can be oriented in either of two ways; e.g., (i) with the —CnH2n— group depicted in Formula I in the 2-position and the carbonyl group in the 4- position, or (ii) with the carbonyl group in the 2-position and the —CnH2n— group in the 4-position.

Particularly preferred compounds are those wherein $R^2$ is hydroxy, $R^3$ is hydrogen, and n has a value of 2; e.g., N-{2-[2-(2-amino-4-hydroxy-5,6,7,8-tetrahydropyrido[2,3-d]pyrimidin-6-yl)ethyl]-pyrrol-5-ylcarbonyl}-L-glutamic acid; N-{2-[2-(2-amino-4-hydroxy-5,6,7,8-tetrahydropyrido[2,3-d]pyrimidin-6-yl)ethyl]-pyrrol-4-ylcarbonyl}-L-glutamic acid; N-{4-[2-(2-amino-4-hydroxy-5,6,7,8-tetrahydropyrido[2,3-d]-pyrimidin-6-yl)ethyl]-pyrrol-2-ylcarbonyl} -L-glutamic acid; N-{3-[2-(2-amino-4-hydroxy-5,6,7,8-tetrahydropyrido[2,3-d]pyrimidin-6-yl)ethyl]-pyrazol-5-ylcarbonyl}-L-glutamic acid; N-{2-[2-(2-amino-4-hydroxy-5,6,7,8-tetrahydropyrido[2,3-d]pyrimidin-6-yl)ethyl]-thiazol-4-ylcarbonyl}-L-glutamic acid; N-{2-[2-(2-amino-4-hydroxy-5,6,7,8-tetrahydropyrido[2,3-d]pyrimidin-6-yl)ethyl]-thiazol-5-ylcarbonyl}-L-glutamic acid; N-{3-[2-(2-amino-4-hydroxy-5,6,7,8-tetrahydropyrido[2,3-d]pyrimidin-6-yl)ethyl]-isothiazol-5-ylcarbonyl}-L-glutamic acid, N-{5-[2-(2-amino-4-hydroxy-5,6,7,8-tetrahydropyrido[2,3-d]pyrimidin-6-yl)ethyl]-isothiazol-3-ylcarbonyl}-L-glutamic acid; N-{2-[2-(2-amino-4-hydroxy-5,6,7,8-tetrahydropyrido[2,3-d]pyrimidin-6-yl)ethyl]-imidazol-4-ylcarbonyl}-L-glutamic acid; N-{2-[2-(2,4-diamino-5,6,7,8-tetrahydropyrido[2,3-d]pyrimidin-6-yl)ethyl]-pyrrol-5-ylcarbonyl} -L-glutamic acid; N-{2-[2-(2,4-diamino-5,6,7,8-tetrahydropyrido[2,3-d]pyrimidin-6-yl)ethyl]-pyrrol-4-ylcarbonyl}-L-glutamic acid; N-{4-[2-(2,4-diamino-5,6,7,8-tetrahydropyrido[2,3-d]-pyrimidin-6-yl)ethyl]-pyrrol-2-ylcarbonyl}-L-glutamic acid; N-{3-[2-(2,4-diamino-5,6,7,8-tetrahydropyrido[2,3-d]pyrimidin-6-yl)ethyl]-pyrazol-5-ylcarbonyl}-L-glutamic acid; N-{2-[2-(2,4-diamino-5,6,7,8-tetrahydropyrido[2,3-d]pyrimidin-6-yl)ethyl]-thiazol-4-ylcarbonyl}-L-glutamic acid; N-{2-[2-(2,4-diamino-5,6,7,8-tetrahydropyrido[2,3-d]pyrimidin-6-yl)ethyl]-thiazol-5-ylcarbonyl}-L-glutamic acid; N-{3-[2-(2,4-diamino-5,6,7,8-tetrahydropyrido[2,3-d]pyrimidin-6-yl)ethyl]-isothiazol-5-ylcarbonyl}-L-glutamic acid; N-{ 5-[2-(2,4-diamino-5,6,7,8-tetrahydropyrido[2,3-d]-pyrimidin-6-yl)ethyl]-isothiazol-3-ylcarbonyl}-L-glutamic acid; and N-{2-[2-(2,4-diamino-5,6,7,8-tetrahydropyrido[2,3-d]pyrimidin-6-yl)ethyl]-imidazol-4-ylcarbonyl}-L-glutamic acid.

The compounds of this invention can be prepared through catalytic hydrogenation of a compound of the formula:

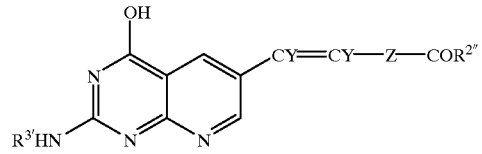

II in which:

Z is as defined above;

$R^{2''}$ is a carboxylic acid protecting group or CH(COR$^{2'}$) CH$_2$CH$_2$COR$^{2'}$ in which $R^{2'}$ s a carboxylic acid protecting group;

$R^{3'}$ is an amino protecting group; and each Y when taken separately is hydrogen or both Y's when taken together are a carbon—carbon bond.

Suitable hydrogenation catalysts include noble metals and noble metal oxides such as palladium or platinum oxide, rhodium oxide, and the foregoing on a support such as carbon or calcium oxide.

When $R^{2''}$ is —CONHCH(COOR$^{2'}$)CH$_2$CH$_2$COOR$^{2'}$, protecting groups encompassed by $R^{2''}$ and $R^{3'}$ are removed. If on the other hand $R^{2''}$ is a carboxylic acid protecting group, the $R^{2''}$ protecting group can removed following hydrogenation as described above, and the resulting free carboxylic acid then coupled with a protected glutamic acid derivative in the manner described in U.S. Pat. No. 4,684, 653, the disclosure of which is incorporated herein by reference, using conventional condensation techniques for forming peptide bonds such as dicyclohexylcarbodiimide or diphenylchlorophosphonate. Following this coupling reaction, any remaining protecting groups are removed.

Protecting groups encompassed by $R^2$, $R^{2'}$, $R^{2''}$, and $R^{3'}$ can be removed through acidic or basic hydrolysis, as for example with sodium hydroxide. Methods of removing the various protective groups are described in the standard references noted above and incorporated herein by reference.

According to the foregoing processes, compounds of Formula II in which $R^1$ is hydroxy are obtained. When a compound of Formula I in which $R^1$ is amino is desired, a compound in which $R^1$ is hydroxy can be treated with 1,2,4-triazole and (4-chlorophenyl)dichlorophosphate and the product of this reaction then treated with concentrated ammonia.

Compounds of Formula II can be prepared utilizing the procedures described in U.S. Pat. No. 4,818,819, the disclosure of which is incorporated herein by reference. In one embodiment a 6-vinyl- or 6-ethynylpyrido[2,3-d]pyrimidine is allowed to react with a halo-Z-carbonyl compound in the presence of a palladium/trisubstituted phosphine catalyst:

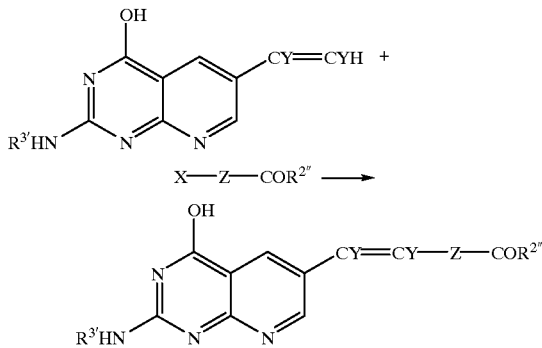

in which each of $R^{2''}$, $R^{3'}$, Y, and Z is as defined above and X is bromo or iodo. The 6-vinyl- and 6-ethynylpyrido[2,3-d]pyrimidine intermediates are known chemical intermediates being described, for example, in U.S. Pat. No. 4,818,819, noted supra.

Alternatively, a 6-bromo- or 6-iodopyrido[2,3-d]pyrimidine intermediate is allowed to react with a vinyl or ethynyl derivative of the heterocycle comprised by Z, again in the presence of the same palladium/trisubstituted phosphine catalyst:

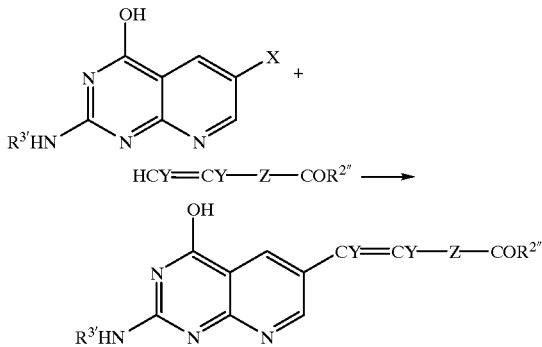

in which each of $R^{2''}$, $R^{3'}$, Y, X, and Z is as defined above. Both the 6-bromo- or 6-iodopyrido[2,3-d]pyrimidine intermediates and palladium/trisubstituted phosphine catalyst again are described in U.S. Pat. No. 4,818,819, noted supra.

The heterocyclic starting materials either are known or can be made through a variety of conventional techniques. For example, vinyl-Z—$COR^{2''}$ intermediates can be obtained from the corresponding aldehydes through treatment with methyltriphenylphosphonium bromide and lithium hexamethyldisilazide in tetrahydrofuran. Alternatively a vinyl-Z—H compound can be carboxylated, as for example with ethyl chloroformate and n-butyllithium. The X—Z—$COR^{2''}$ compounds can be obtained through halogenation of a heterocylic carboxylate, e.g., H—Z—$COR^{2''}$, utilizing conventional halogenation reagents such as N-bromosuccinimide or N-iodosuccinimide. In any of these routes, compounds carrying a substitutable ring nitrogen atom in the heterocyclic system can be protected through prior formation of the corresponding N-trityl compound or N-triisopropylsilyl compound.

The compounds of this invention have an effect on one or more enzymes which utilize folic acid, and in particular metabolic derivatives of folic acid, as a substrate.

The action of the compounds appear to be similar in this regard to that of 5,10-dideazatetrahydrofolic acid which is described in U.S. Pat. No. 4,684,653. Thus the compounds exhibit particularly strong inhibitory activity against the enzyme glycinamide ribonucleotide formyltransferase. The compounds also exhibit inhibitory activity against folate enzymes such as dihydrofolate reductase and thymidylate synthetase. Representative $IC_{50}$ values for example against human T-cell derived lymphoblastic leukemia cells (CCRF-CEM), for (i) N-{4-[2-(2-amino-4-hydroxy-5,6,7,8-tetrahydropyrido[2,3-d]pyrimidin-6-yl)ethyl]-pyrrol-2-ylcarbonyl}-L-glutamic acid, (ii) N-{ 2-[2-(2-amino-4-hydroxy-5,6,7,8-tetrahydropyrido[2,3-d]pyrimidin-6-yl)ethyl]-pyrrol-4-ylcarbonyl}-L-glutamic acid, (iii) N-{2-[2-(2-amino-4-hydroxy-5,6,7,8-tetrahydropyrido[2,3-d]pyrimidin-6-yl)ethyl]-pyrrol-5-ylcarbonyl}-L-glutamic acid, and (iv) N-{3-[2-(2-amino-4-hydroxy-5,6,7,8-tetrahydropyrido[2,3-d]pyrimidin-6-yl)ethyl]-pyrazol-5-ylcarbonyl}-L-glutamic acid are (i) 0.024 $\mu$/mL, (ii) 0.008 $\mu$/mL, (iii) 0.009 $\mu$/mL, and (iv) 0.0019 $\mu$/mL.

The compounds can be used, under the supervision of qualified professionals, to inhibit the growth of neoplasms including choriocarcinoma, leukemia, adenocarcinoma of the female breast, epidermic cancers of the head and neck, squamous or small-cell lung cancer, and various lymphosarcomas. The compounds can also be used to treat mycosis fungoides, arthritis, and psoriasis. The compounds can be administered orally but preferably are administered parenterally, alone or in combination with other therapeutic agents including other anti-neoplastic agents, steroids, etc., to a mammal suffering from neoplasm and in need of treatment. Parenteral routes of administration include intramuscular, intrathecal, intravenous and intra-arterial. Dosage regimens must be titrated to the particular neoplasm, the condition of the patient, and the response but generally doses will be from about 10 to about 100 mg/day for 5–10 days or single daily administration of 250–500 mg, repeated periodically; e.g. every 14 days. While having a low toxicity as compared to other antimetabolites now in use, a toxic response often can be eliminated by either or both of reducing the daily dosage or administering the compound on alternative days or at longer intervals such as every three days. Concomitant administration of folic acid as a rescue therapy also may be indicated. Oral dosage forms include tablets and capsules containing from 1–10 mg of drug per unit dosage. Isotonic saline solutions containing 20–100 mg/mL can be used for parenteral administration.

The following examples will serve to further illustrate the invention.

Methods and Materials

Tetrahydrofuran was distilled from sodium/benzophenone; dimethylformamide and acetonitrile were distilled over calcium hydride. All reactions in these solvents were conducted under positive pressure of an inert gas. Column chromatography was carried out with Merck grade 60 silica gel (230–400 mesh). NMR spectra (250 or 300 MHz) were recorded using $CDCl_3$, $CD_3OD$, or DMSO-$d_6$ as solvents and internal standards. In the NMR data, "s" denotes singlet, "d" denotes doublet, "t" denotes triplet, "q" denotes quartet, "m" denotes multiplet, and "br" denotes a broad peak. Melting points are uncorrected.

EXAMPLE 1

Methyl 4-[2-(2-pivaloylamino-4-hydroxypyrido[2,3-d]pyrimidin-6-yl)ethynyl]-1-tri-isopropylsilylpyrrole-2-carboxylate A mixture of 3-iodo-5-methoxycarbonyl-1-triisopropylsilylpyrrole (1.222 g, 3.0 mmol), 2-pivaloylamino-4-hydroxy-6-ethynylpyrido[2,3-d] pyrimidine (0.851 g, 3.15 mmol), Pd(PPh)$_2$C$_{12}$ (105 mg, 0.15 mmol), cuprous iodide (2 g mg, 0.15 mmol), and triethylamine (0.5 mL) in acetonitrile (50 mL) was heated at reflux for 4 hours. The resulting solution was cooled, filtered, and concentrated in vacuo. The residue was purified by flash chromatography, eluting with hexanes:ethyl acetate (2:1). The first major fraction is unchanged starting material (270 mg, 32%); the subsequent major fluorescent fractions were combined and concentrated in vacuo to give methyl 4-[2-(2-pivaloylamino-4-hydroxypyrido[2,3-d]pyrimidin-6-yl)ethynyl]1-triisopropylsilylpyrrole-2-carboxylate as a pale yellow solid (935 mg, 57%, mp 163–165° C.): $^1$H NMR (CDCl$_3$) δ 8.90 (br s, 1H), 8.52 (d, 1H, J=2.4 Hz), 7.35 (d, 1H, J=1.4 Hz), 7.23 (d, 1H, J=1.4 Hz), 3.79 (s, 3H), 1.75 (sept, 3H, J=7.6 Hz), 1.31 (s, 9H), 1.10(d, 18H, J=7.6 Hz).

Anal. Calcd for C$_{29}$H$_{39}$N$_5$O$_4$Si: C, 63.36; H, 7.15; N, 12.74. Found: C, 63.14; H, 7.12; N, 12.62.

The 3-iodo-5-methoxycarbonyl-1-triisopropylsilylpyrrole starting material can be prepared as follows. Sodium hydride (80% dispersion; 660 mg, 22 mmol) was washed with pentane and suspended in tetrahydrofuran (20 mL). A solution of methyl pyrrole-2-carboxylate (1.251 g, 10 mmol) in tetrahydrofuran (10 mL) was added and the mixture stirred at room temperature. When gas evolution ceased, triisopropylsilyl chloride (1.928 mg, 10 mmol) was added dropwise, and the mixture was stirred for 1 hour, heated at reflux overnight, and partitioned between ether and water. The ethereal layer was dried (magnesium sulfate) and concentrated in vacuo. The residue was purified by chromatography using hexanes:ethyl acetate (8:1) to yield 2-methoxycarbonyl-1-triisopropylsilylpyrrole as an oil (2.05 g, 73%): $^1$H NMR (CDCl$_3$) δ 7.12 (m, 2H), 6.26 (m, 1H), 3.78 (m, 3H), 1.76 (sept, 3H, J=7.6 Hz), 1.04 (d, 18 H, J=7.6 Hz).

Anal. Calcd for C$_5$H 27NO 2Si: C, 64.01; H, 9.67; N, 4.98. Found: C, 64.30; H, 9.96, N, 4.72.

N-Iodosuccinimide (653 mg, 2.9 mmol) was added to a stirred solution of 2-methoxycarbonyl-1-triisopropylsilylpyrrole (815 g, 2.9 mmol) in tetrahydrofuran (20 mL). The reaction mixture was stirred at room temperature for two days. The solvent was then removed in vacuo and the oily residue suspended in hexanes (50 mL) with vigorous stirring. The insoluble solid was removed by filtration and the filtrate concentrated in vacuo. Purification of the residue by column chromatography using hexanes gave 3-iodo-5-methoxycarbonyl-1-triisopropylsilylpyrrole (1.044 g, 88%) as a white crystalline solid, mp 81–83° C.: $^1$H NMR (CDCl$_3$) δ 7.18 (d, 1H, J=1 5 Hz), 7.09 (d, 1H, J=1.5 Hz), 379 (s, 3H), 1.74 (sept, 3H, J=7.6 Hz), 1.11 (d, 18H, J=7.6 Hz).

Anal. Calcd for C$_{15}$H$_{26}$INO$_2$Si: C, 44.23; H, 6.43; N, 3.44. Found: C, 44.00; H, 6.53; N, 3.43.

EXAMPLE 2

Methyl 4-[2-(2-Pivaloylamino-4-hydroxy-5,6,7,8-tetrahydropyrido[2,3-d]-pyrimidin-6-yl)ethyl]-1-triisopropylsilylpyrrole-2-carboxylate A mixture of methyl 4-[2-(2-pivaloylamino-4-hydroxypyrido[2,3-d]pyrimidin-6-yl)ethynyl]-1-triisopropylsilylpyrrole-2-carboxylate (550 mg, 1.0 mmol) and 10% palladium-on-carbon (220 mg) in methanol (45 mL) was stirred overnight under hydrogen (50 psi). The reaction mixture was filtered through Celite and the filtrate concentrated in vacuo. The residue was dissolved in methylene chloride and filtered through a short silica gel column. The eluate was evaporated to give methyl 4-[2-(2-pivaloylamino-4-hydroxy-5,6,7,8-tetrahydropyrido[2,3-d] pyrimidin-6-yl)ethyl]-1-triisopropylsilylpyrrole-2-carboxylate (524 mg, 94%). The analytical sample, mp 202–204° C., was obtained by column chromatography using chloroform:methanol (19:1): $^1$H NMR (CDCl$_3$) δ 11.34 (br s, 1H), 7.85 (br s, 1H), 6.98 (s, 1H), 6.90 (s, 1H), 4.69 (s, 1H), 3.79 (s, 3H), 3.36 (br d, 1H, J=10.0 Hz), 2.99 (m, 1H), 2.83 (m, 1H), 2.59 (m, 2H), 2.12 (dd, 1H, J=15.6, 9.0 Hz), 1.90–1.50 (m, 6H), 1.30 (s, 9H), 1.11 (d, 18H, J=7.6 Hz).

Anal. Calcd for C$_{29}$H$_{47}$N 504Si: C, 62.15; H, 8.49; N, 12.42. Found: C, 62.15; H, 8.54; N, 12.42.

EXAMPLE 3

Ethyl 5-[2-(2-Pivaloylamino-4-hydroxy-5,6,7,8-tetrahydropyrido[2,3-d]-pyrimidin-6-yl)ethyl] pyrazole-3-carboxylate Reduction of ethyl 5-[2-(2-pivaloylamino-4-hydroxypyrido[2,3-d]pyrimidin-6-yl)ethenyl]pyrazole-3-carboxylate (820 mg, 2.0 mmol) using palladium-on-carbon (820 mg) as catalyst as in Example 2 similarly yields ethyl 5-[2-(2-pivaloylamino-4-hydroxy-5,6,7,8-tetrahydropyrido [2,3-d]pyrimidin-6-yl)ethyl]pyrazole-3-carboxylate, mp 235–237° C.: $^1$H NMR (DMSO-d$_6$) δ 13.25 (s, 1H), 11.22 (s, 1H), 10.67 (s, 1H), 6.47 (s, 1H), 6.45 (s, 1H), 4.22 (q, 2H, J=7.0 Hz), 3.36 (brd, 1H, J=107 Hz), 2.83 (m, 1H), 2.69 (m, 2H), 2.54 (brd, 1H, J=15.2 Hz), 1.90 (dd, 1H, J=15.2, 7.9 Hz), 1.72–1.50 (m, 3H), 1.26 (t, 3H, J=7.0 Hz), 1.25 (s, 9H). HRMS calcd for C$_{20}$H$_{28}$N$_6$O$_4$ 416.2172, found 416.2179.

Anal. Calcd for C$_{20}$H$_{27}$N$_6$O$_4$: C, 57.82; H, 6.55; N, 20.23. Found: C, 57.64; H, 6.58 N, 20.61.

EXAMPLE 4

Methyl 5-[2-(2-Pivaloylamino-4-hydroxypyrido[2,3-d]pyrimidin-6-yl)ethenyl]pyrrole-2-carboxylate A mixture of methyl 5-vinylpyrrole-2-carboxylate (298 mg, 2.0 mmol), 2-pivaloylamino4-hydroxy-6-bromopyrido [2,3-d]pyrimidine (683 mg, 2.1 mmol), palladium acetate (22.5 mg, 0.1 mmol), tri-o-tolylphosphine (60.9 mg, 0.2 mmol), and triethylamine (7.0 mL) in acetonitrile (20 mL) was heated overnight at reflux. The reaction mixture was cooled to room temperature, and the solid which formed collected by filtration, washed with cold acetonitrile, and dried to give methyl 5-[2-(2-pivaloylamino-4-hydroxypyrido[2,3-d]pyrimidin-6-yl)ethenyl]pyrrole-2-carboxylate as a yellow solid (706 mg, 89%). The product can be used in the next step without further purification. An analytical sample, mp >260° C., was obtained by recrystallization from methanol: $^1$H NMR (DMSO-d$_6$) δ 12.28 (s, 1H), 12.08 (s, 1H), 11.40 (s, 1H), 8.93 (s, 1H), 8.40 (s, 1H), 7.36 (d, 1H, J=16.6 Hz), 7.27 (d, 1H, J=16.6 Hz), 6.81 (m, 1H), 6.48 (m, 1H), 3.76 (s, 3H), 1.23 (s, 9H).

Anal. Calcd for C$_{20}$H$_{21}$N$_5$O$_4$: C, 60.75; H, 5.35; N, 17.71. Found: C, 60.80; H, 5.36; N, 17.92.

EXAMPLE 5

Methyl 4-[2-(2-Pivaloylamino-4-hydroxypyrido[2,3-d]pyrimidin-6-yl)-ethenyl]-pyrrole-2-carboxylate Similarly obtained from methyl 4-vinylpyrrole-2-carboxylate (298 mg, 2.0 mmol), 2-pivaloylamino-4-hydroxy-6-bromopyrido[2,3-d]pyrimidine (715 mg, 2.2 mmol), palladium acetate (27 mg, 0.1 mmol), tri-o-tolylphosphine (61 mg, 0.2 mmol), and triethylamine (1.4 mL) according to the procedure of Example 4 is methyl 4-[2-(2-pivaloylamino4-hydroxypyrido[2,3-d]pyrimidin-6-yl)ethenyl]pyrrole-2-carboxylate (700 mg, 89%): mp >260° C.: $^1$H NMR (DMSO-d$_6$) δ 12.30 (br s, 1H), 12.06 (s, 1H), 11.39 (s, 1H), 8.98 (s, 1H), 8.41 (s, 1H), 7.31 (d, 1H, J=16.5 Hz), 7.26 (s, 1H), 7.11 (s, 1H), 7.15 (d, 1H, J=16.5 Hz), 3.76 (s, 3H), 1.25 (s, 9H).

Anal. Calcd for $C_{20}H_{21}N_5O_4.0.5 H_2O$: C, 59.38; H, 5.49; N, 17.32. Found: C, 59.24; H, 5.33; N, 17.37.

EXAMPLE 6

Methyl 5-[2-(2-Pivaloylamino-4-hydroxypyrido[2,3-d]pyrimidin-6-yl)ethenyl]pyrrole-3-carboxylate Use of methyl 5-vinylpyrrole-3-carboxylate in the same fashion as Example 4 yields methyl 5-[2-(2-pivaloylamino-4-hydroxypyrido[2,3-d]pyrimidin-6-yl)ethenyl]-pyrrole-3-carboxylate (1.02 g, 86%) mp >260° C.: $^1$H NMR (DMSO-d$_6$) δ 11.95 (br s, 1H), 11.06 (s, 1H), 9.76 (s, 1H), 8.86 (s, 1H), 8.33 (s, 1H), 7.51 (s, 1H), 7.20 (d, 1H, J=16.4 Hz), 7.03 (d, 1H, J=16.4 Hz), 6.64 (s, 1H), 3.69 (s, 3H), 1.2:2 (s, 9H).

Anal. Calcd for $C_{20}H_{21}N_5O_4$: C, 60.75; H, 5.35 N, 17.71. Found: C, 60.50; H, 5.27; N, 17.76.

The methyl 5-vinylpyrrole-2-carboxylate starting material is obtained as follows. To a stirred suspension of methyltriphenylphosphonium bromide (2.358 g, 6.6 mmol) in tetrahydrofuran (50 mL) was added dropwise 1 N lithium hexamethyldisilazide in tetrahydrofuran (6.6 mL, 6.6 mmol) at 0° C. After the solution was stirred for 1 hour, methyl 5-formylpyrrole-2-carboxylate (453 mg, 3.0 mmol) was added in one portion to the resulting solution, and the reaction mixture was stirred for 1.5 hours at room temperature, quenched by addition of water (10 mL) and then acidified with 1 N HCl. The organic phase was dried (magnesium sulfate) and concentrated. Purification of the residue by flash chromatography using hexanes:ethyl acetate (4:1) gave methyl 5-vinylpyrrole- 2-carboxylate (400 mg, 90%) as a white crystalline solid, mp 91–93° C.: $^1$H NMR (CDCl$_3$) δ 9.40 (br s, 1H), 6.86 (dd, 1H, J=3.7, 2.4 Hz), 6.56 (dd, 1H, J=17.8, 11.2 Hz), 6.27 (dd, 1H, J=3.7, 2.8 Hz), 5.59 (d, 1H, J=17.8 Hz), 5.22 (d, 1H, 11.2 Hz), 3.85 (s, 3H).

Anal. Calcd for $C_8H_9NO_2$: C, 63.56; H, 6.00; N, 9.27. Found: C, 63.33; H, 6.28; N, 9.00.

Similarly obtained from methyl 4-formylpyrrole-2-carboxylate (453 mg, 3.0 mmol) and methyltriphenylphosphonium bromide (2.36 g, 6.6 mmol) is methyl 4-vinylpyrrole-2-carboxylate as a white crystalline solid (436 mg, 98%, mp 63–65° C.): $^1$H NMR (CDCl$_3$) δ 9.34 (br s, 1H), 7.00 (m, 1H), 6.94 (s, 1H), 6.54 (dd, 1H, J=17.7, 11.0 Hz), 5.43 (dd, 1H, J=17.7, 1.2 Hz), 5.02 (dd, 1H, J=11.0, 1.2 Hz).

Anal. Calcd for $C_9H_9NO_2$: C, 63.56; H, 6.00; N, 9.27. Found: C, 63.38; H, 6.08; N, 9.27.

Similarly obtained from methyl 5-formylpyrrole-3-carboxylate (907 mg, 6 mmol) and methyltriphenylphosphonium bromide (5.71 g, 13.2 mmol) is methyl 5-vinylpyrrole-3-carboxylate, mp 97–99° C.: $^1$H NMR (CDCl$_3$) δ 8.83 (br s, 1H), 7.36 (s, 1H), 6.59 (s, 1H), 6.56 (dd, 1H, J=17.7, 11.2 Hz), 5.35 (d, 1H, J=17.7 Hz),5.11 (d, 1H, J=11.2 Hz), 3.81 (s, 3H).

Anal. Calcd for $C_8H_9NO_2$: C, 63.56; H, 6.00; N, 9.27. Found: C, 63.35; H, 6.10; N, 9.20.

Similarly prepared from ethyl 5-formylpyrazole-3-carboxylate (1.66 g, 10 mmol) and methyltriphenylphospho-nium bromide (7.50 g, 21 mmol) is ethyl 5-vinylpyrazole-3-carboxylate as a white crystalline solid (1.55 g, 95%), mp 75–77° C.; 111 NMR (CDCl$_3$) δ 11.20 (br s, 1H), 6.89 (s, 1H), 6.68 (dd, 1H, J=17.7, 11.3 Hz), 5.76 (d, 1H, J=17.7 Hz), 5.38 (d, 1H, J=11.3 Hz), 4.37 (q, 2H, J=7.2 Hz), 1.37 (t, 3H, J=7.2 Hz).

Anal. Calcd for $C_8H_{10}N_2O_2$: C, 57.82; H, 6.07; N, 16.86. Found: C, 57.66; H, 6.21; N, 17.05.

EXAMPLE 7

Ethyl 5-[2-(2-pivaloylamino-4-hydroxypyrido[2,3-d]pyrimidin-6-yl)ethenyl]pyrazole-3-carboxylate From ethyl 5-vinylpyrazole-3-carboxylate (492 mg, 3.0 mmol), 2-pivaloylamino-4-hydroxy-6-bromopyrido[2,3-d]pyrimidine (25, 1.07 g, 3.3 mmol), palladium acetate (34 mg, 0.15 mmol), tri-o-tolylphosphine (91 mg, 0.3 mmol), and triethylamine (2.1 mL) there is similarly obtained according to the procedure of Example 4, ethyl 5-[2-(2-pivaloylamino4-hydroxypyrido[2,3-d]pyrimidin-6-yl) ethenyl]pyrazole-3-carboxylate (1.04 g, 85%, mp >260° C.); $^1$H NMR (DMSO-d$_6$) δ 13.75 (s, 1H), 12.28 (s, 1H), 11.42 (s, 1H), 9.01 (s, 1H), 8.47 (d, 1H, J=2.5 Hz), 7.36 (AB, 2H), 6.96 (s, 1H), 4.29 (q, 2 H, J=7.0 Hz), 1.30 (t, 3H, J=7.0 Hz), 1.25 (s, 9H). HRMS calcd for $C_{20}H_{22}N_6O_4$ 410.1703, found 410.1692.

Anal. Calcd for $C_{20}H_{21}N_6O_4$: C, 58.67; H, 5.17; N, 20.53. Found: C, 58.50; H, 5.13 N, 20.44.

EXAMPLE 8

Methyl 5-[2-(2-Pivaloylamino-4-hydroxy-5,6,7,8-tetrahydropyrido[2,3-d]-pyrimidin-6-yl)ethyl]pyrrole-2-carboxylate A mixture of methyl 5-[2-(2-pivaloylamino-4-hydroxypyrido[2,3-d]-pyrimidin-6-yl)ethenyl]pyrrole-2-carboxylate (593 mg, 1.5 mmol) and platinum oxide (68 mg) in glacial acetic acid (200 mL) was stirred overnight under hydrogen (50 psi). The reaction mixture was filtered through Celite and the filtrate was concentrated in vacuo. The solid was recrystallized from methanol to give methyl 5-[2-(2-pivaloylamino-4-hydroxy-5,6,7,8-tetrahydropyrido[2,3-d]pyrimidin-6-yl)ethyl]pyrrole-2-carboxylate as an off-white solid (505 mg, 84%), mp 246–248° C.: $^1$H NMR (DMSO-d$_6$) δ 11.67 (s, I H), 10.90 (br s, 1H), 10.60 (br s, 1H), 6.66 (s, 1H), 6.45 (s, 1H), 5.91 (s, 1H), 3.72 (s, 3H), 3.22 (brd, 1H, J=10.5 Hz), 2.81 (m, 1H), 2.64 (m, 2H), 2.52 (brd, 1H, J=15.2 Hz), 1.88 (dd, 1H, J=15.2, 7.9 Hz), 1.68–1.50 (m, 3H), 1.21 (s, 9H).

Anal. Calcd for $C_{20}H_{27}N_5O_4$: C, 59.84; H, 6.78; N, 17.44. Found: C, 59.55; H, 6.79; N, 17.20.

EXAMPLE 9

Methyl 4-[2-(2-Pivaloylamino-4-hydroxy-5,6,7,8-tetrahydropyrido[2,3-d]-pyrimidin-6-yl)ethyl]pyrrole-2-carboxylate Upon reduction of methyl 4-[2-(2-pivaloylamino-4-hydroxypyrido[2,3-d]-pyrimidin-6-yl)ethenyl]pyrrole-2-carboxylate with hydrogen and palladium-on-carbon catalyst (200 mg) analogously to that described in Example 8, there is obtained methyl 4-[2-(2-pivaloylamino-4-hydroxy-5,6,7,8-tetrahydropyrido[2,3-d]pyrimidin-6-yl)ethyl] pyrrole-2-carboxylate (380 mg, 95%): mp 236–238° C.: $^1$H NMR (DMSO-d$_6$) δ 11.59 (s, 1H), 11.21 (s, 1H), 10.60 (s, 1H), 6.81 (s, 1H), 6.62 (s, 1H), 6.42 (s, 1H), 3.70 (s, 3H), 3.23 (br d, 1H, J=10.5 Hz), 2.82 (m, 1H), 2.57–2.43 (m, 3H), 1.87 (dd, 1H, J=15.2, 8.0 Hz), 1.68–1.43 (m, 3H), 1.18 (s, 9H).

Anal. Calcd for $C_{20}H_{27}N_5O_4$: C, 59.84; H, 6.78; N, 17.44. Found: C, 59.70; H, 6.61; N, 17.65.

EXAMPLE 10

Methyl 5-[2-(2-Pivaloylamino-4-hydroxy-5,6,7,8-tetrahydropyrido[2,3-d]-pyrimidin-6-yl)ethyl] pyrrole-3-carboxylate Similarly prepared as in Example 8 but from methyl 5-[$^2$-(2-pivaloylamino-4-hydroxypyrido[2,3-d]pyrimidin-6-yl)ethanyl]pyrrole-3-carboxylate is methyl 5-[2-(2-pivaloylamino-4-hydroxy-5,6,7,8-tetrahydropyrido[2,3-d]pyrimidin-6-yl)ethyl]pyrrole-3-carboxylate, mp >260° C.: $^1$H NMR (CDCl$_3$/CD$_3$OD, 1/1) δ 7.22 (s, 1H), 6.20 (s, 1H), 3.71 (s, 3H), 3.28 (br d, 1H, J=12.1 Hz), 2.91 (dd, 1H, J=12.1, 8.7 Hz), 2.75–2.55 (m, 3H), 2.00 (dd, 1H, J=15.8, 9.0 Hz), 1.74 (m, 1H), 1.61 (m, 1H), 1.21 (s, 9H).

Anal. Calcd for $C_{20}H_{27}N_5O_4 \cdot 0.5\ H_2O$: C, 58.51; H, 6.88; N, 17.07. Found: C, 58.55; H, 6.95; N, 16.90.

EXAMPLE 11

4-[2-(2-Amino-4-hydroxy-5,6,7,8-tetrahydropyrido [2,3-d]pyrimidin-6-yl)ethyl]pyrrole-2-carboxylic Acid A suspension of methyl 4-[2-(2-pivaloylamino-4-hydroxy-5,6,7,8-tetrahydropyrido[2,3-d]pyrimidin-6-yl) ethyl]-1-triisopropylsilylpyrrole-2-carboxylate (390.4 mg, 0.7 mmol) in 1N sodium hydroxide (1 mL) was heated under reflux until clear (about 4 hours). The mixture was cooled to room temperature, extracted with ethyl acetate, and then acidified with glacial acetic acid. The solid which formed was collected by filtration, washed with water, and dried in vacuo to give 4-[2-(2-amino-4-hydroxy-5,6,7,8-tetrahydropyrido[2,3-d]pyrimidin-6-yl)ethyl]pyrrole-2-carboxylic acid (199 mg, 94%), mp >260° C.: $^1$H NMR (DMSO-d$_6$) δ 11.39 (s, 1H), 9.72 (br s, 1H), 6.73 (s, 1H), 6.55 (s, 1H), 6.25 (s, 1H), 5.93 (s, 2H), 3.16 (br d, 1H, J=9.5 Hz), 2.72 (m, 1H), 2.43 (m, 3H), 1.75 (m, 1H), 1.42–1.53 (m, 3H); $^1$H NMR (CD$_3$OD) δ 6.69 (s, 1H), 6.63 (s, 1H), 3.31 (brd, 1H, J=12.1 Hz), 2.91 (dd, 1H, J=12.1, 9.2 Hz), 2.67 (dd, 1H, J=15.3, 4.4 Hz), 2.55 (m, 2H), 1.99 (dd, 1H, J=15.3, 9.4 Hz), 1.76 (m, 1H), 1.60 (m, 2H).

Anal. Calcd for $C_{14}H_{17}N_5O_3$: C, 55.44; H, 5.65; N, 23.09. Found: C, 55.44; H, 5.84; N, 23.49.

EXAMPLE 12

5-[2-(2-Amino-4-hydroxy-5,6,7,8-tetrahydropyrido [2,3-d]pyrimidin-6-yl)ethyl]pyrrole-2-carboxylic Acid In the same manner as Example 11 there is obtained from methyl 5-[2-(2-pivaloylamino4-hydroxy-5,6,7,8-tetrahydropyrido[2,3-d]pyrimidin-6-yl)ethyl]pyrrole-2-carboxylate (401 mg, 1.0 mmol) and 1N sodium hydroxide (6 mL), 5-[2-(2-amino-4-hydroxy-5,6,7,8-tetrahydropyrido [2,3-d]pyrimidin-6-yl)ethyl]pyrrole-2-carboxylic acid (257 mg, 85%) as an off-white solid, mp >260° C.: $^1$H NMR (DMSO-d$_6$) δ 11.34 (s, 1H), 10.20 (br s, 1H), 6.50 (s, 1H), 6.25 (s, 1H), 5.96 (s, 2H), 5.87 (s, 1H), 3.15 (br d, 1H, J=10.3 Hz), 2.73 (m, 1H), 2.63 (m, 2H), 2.55 (br d, 1H, J=14.9 Hz), 1.78 (dd, 1H, J=14.9, 7.9 Hz), 1.80–1.50 (m, 3H).

Anal. Calcd for $C_{14}H_{17}N_5O_3 \cdot 0.5H_2O$: C, 53.82H, 5.81; N, 22.43. Found: C, 54.13; H, 5.65; N, 22.19.

EXAMPLE 13

5-[2-(2-Amino-4-hydroxy-5,6,7,8-tetrahydropyrido [2,3-d]pyrimidin-6-yl)ethyl]pyrrole-3-carboxylic Acid Upon saponification of methyl 5-[2-(2-pivaloylamino-4-hydroxy-5,6,7,8-tetrahydropyrido[2,3-d]pyrimidin-6-yl) ethyl]pyrrole-3-carboxylate (401 mg g, 1.0 mmol) with 1N sodium hydroxide (15 mL) as described in Example 11, there is obtained 5-[2-(2-amino-4-hydroxy-5,6,7,8-tetrahydropyrido[2,3-d]pyrimidin-6-yl)ethyl]pyrrole-3-carboxylic acid, mp >260° C.: $^1$H NMR (DMSO-d$_6$) δ 11.49 (s, 1H), 10.12 (br s, 1H), 9.66 (s, 1H), 7.16 (s, 1H), 6.23 (s, 1H), 6.05 (s, 2H), 5.90 (s, 1H), 3.16 (brd, 1H, J=10.9 Hz), 2.78 (m, 1H), 2.63–2.40 (m, 2H), 1.77 (dd, 1H, J=15.2, 8.6 Hz), 1.69–1.43 (m, 3H).

EXAMPLE 14

5-[2-(Amino-4-hydroxy-5,6,7,8-tetrahydropyrido[2, 3-d]pyrimidin-6-yl)ethyl]pyrazole-3-carboxylic Acid Upon saponification of ethyl 5-[2-(2-pivaloylamino-4-hydroxy-5,6,7,8-tetrahydropyrido[2,3-d]pyrimidin-6-yl) ethyl]pyrazole-3-carboxylate (637 mg, 1.5 mmol) with 1N sodium hydroxide (3 mL) as described in Example 11, there is obtained 5-[2-(amino-4 -hydroxy-5,6,7,8-tetrahydropyrido[2,3-d]pyrimidin-6-yl)ethyl]pyrazole-3-carboxylic acid (368 mg, 80%, mp >260° C.): $^1$H NMR (DMSOd$_6$) δ 12.90 (br s, 1H), 9.85 (br s, 1H), 6.67 (s, 1H), 6.42 (s, 1H), 6.27 (s, 1H), 5.96 (s, 2H), 3.16 (br d, 1H, J=107 Hz), 2.74 (m, 1H), 2.65 (m, 1H), 2.46 (brd, 1H, J=15.0 Hz), 1.90 (dd, 1H, J=15.0, 7.9 Hz), 1.68–1.47 (m, 3H).

Anal. Calcd for $C_{13}H_{16}N_6O_3 \cdot 1.5\ H_2O$: C, 47.13; H, 5.78; N, 25.36. Found: C, 46.82; H, 5.78 N, 24.97.

EXAMPLE 15

Dimethyl N-{4-[2-(Amino-4-hydroxy-5,6,7,8-tetrahydropyrido[2,3-d]pyrimidin-6yl)ethyl]pyrrol-2-ylcarbony}-L-glutamate A solution of 4-[2-(2-amino-4-hydroxy-5,6,7,8-tetrahydropyrido[2,3-d]pyrimidin-6yl)ethyl]pyrrole-2-carboxylic acid (152 mg, 0.5 mmol), 2-chloro-4,6-dimethoxy-1,3,5-triazine (98 mg, 0.55 mmol), and 4-methylmorpholine (0.066 mL, 0.6 mmol) in DMF (3 mL) was stirred at room temperature for 2 hours. Dimethyl L-glutamate hydrochloride (0.116 g, 0.55 mmol) and 4-methylmorpholine (0.066 mL, 0.6 mmol) were sequentially added and the mixture was stirred overnight at room temperature. The solvent was removed in vacuo, and the residue chromatographed using chloroform:methanol (9:1) to give dimethyl N-{4-[2-(amino-4-hydroxy-5,6,7,8-tetrahydropyrido[2,3-d]pyrimidin-6-yl)ethyl]pyrrol-2-ylcarbonyl}-L-glutamate (152 mg, 66%) as a white solid, mp 151–153° C.: $^1$H N (CDCl$_3$/1 drop CD$_3$OD) δ 10.20 (br s, 1H), 7.27 (s, 1H, J=7.9 Hz), 6.70 (s, 1H), 6.82 (s, 1H), 5.83 (br s, 2H), 5.38 (br s, 1H), 4.80 (m, 1H), 3.84 (s, 3H), 3.73 (s, 3H), 3.42 (br d, 1H, J=10.1 Hz), 3.05 (m, 1H), 2.76 (dd, 1H, J=15.0, 4.4 Hz), 2.65 (m, 2H), 2.56 (m, 2H), 2.36 (m, 1H), 2.14 (m, 2H), 1.91 (m, 1H), 1.68 (m, 2H).

Anal. Calcd for $C_{21}H_{28}N_6O_6 \cdot 1.5H_2O$: C, 53.71; H, 6.23; N, 17.91. Found: C, 53.34; H, 6.12; N, 18.03.

EXAMPLE 16

Dimethyl N-{5-[2-(2-Amino-4-hydroxy-5,6,7,8-tetrahydropyrido-[2,3-d]-pyrimidin-6-yl)ethyl] pyrrol-2-ylcarbonyl}-L-glutamate Similarly obtained from 5-[2-(2-amino-4-hydroxy-5,6,7, 8-tetrahydropyrido-[2,3-d]pyrimidin-6-yl)ethyl]pyrrole-2- carboxylic acid (227.5 mg g, 0.75 mmol), 2-chloro-4,6-dimethoxy-1,3,5-triazine (145 mg, 0.825 mmol), 4-methylmorpholine (0.20 mL, 1.8 mmol), and dimethyl L-glutamate hydrochloride (191 mg, 0.9 mmol) according to the method of Example 15 is dimethyl N-{5-[2-(2-amino-4-hydroxy-5,6,7,8-tetrahydropyrido[2,3-d]pyrimidin-6-yl) ethyl]pyrrol-2-ylcarbonyl}-L-glutamate as a pale yellow solid after flash column chromatography using chloroform: methanol (4:1). The analytical sample, mp 200–202° C., was recrystallized from methanol: $^1$H NMR (CD$_3$OD) δ 6.85 (d, 1H, J=3.7 Hz), 6.03 (d, 1H, J=3.7 Hz), 4.69 (m, 1H), 3.81 (s, 3H), 3.72 (s, 3H), 3.40 (m, 1H), 3.02 (m, 1H), 2.87–2.60 (m, 3H), 2.56 (m, 2H), 2.34 (m, 1H), 2.40–2.07 (m, 2H), 1.84 (m, 1H), 1.77(m, 2H). Anal. Calcd for C$_{21}$H$_{29}$N$_6$O$_6$.0.5 H$_2$O: C, 53.71; H, 6.23; N, 17.91. Found: C, 53.48; H, 6.08; N, 18.02.

EXAMPLE 17

Dimethyl N-{5-[2-(Amino-4-hydroxy-5,6,7,8-tetrahydropyrido[2,3-d]pyrimidin-6-yl)ethyl]pyrrol-3-ylcarbonyl}-L-glutamate From 5-[2-(2-amino-4-hydroxy-5,6,7,8-tetrahydropyrido [2,3-d]pyrimidin-6-yl)-ethyl]pyrrole-3-carboxylic acid (228 mg, 0.75 mmol), 2-chloro-4,6-dimethoxy-1,3,5-triazine (145 mg, 0.825 mmol), 4-methylmorpholine (0.20 mL, 1.8 mmol), and dimethyl L-glutamate hydrochloride (191 mg, 0.9 mmol) there is obtained according to the procedure of Example 15, dimethyl N-{5-[2-(amino-4-hydroxy-5,6,7,8-tetrahydropyrido[2,3-d]pyrimidin-6-yl)ethyl]pyrrol-3-ylcarbonyl}-L-glutamate as a white solid (184 mg, 53%) after flash column chromatography (chloroform: methanol, 4:1): $^1$H NMR (CD$_3$OD) δ 7.25 (d, 1H, J=1.7 Hz), 6.30 (d, 1H, J=1.7 Hz), 4.58 (m, 1H), 3.71 (s, 3H), 3.63 (s, 3H), 3.33 (m, 1H), 2.92 (dd, 1H, J=12.2, 8.5 Hz), 2.71-2.60 (m, 3H), 2.45 (t, 2H, J=7.3 Hz), 2.22 (m, 1H), 2.09–1.96 (m, 2H), 1.76 (m, 1H), 1.66 (m, 2H).

Anal. Calcd for C$_{21}$H$_{28}$N$_6$O$_6$.1.5 H$_2$O: C, 51.74; H, 6.41; N, 17.24. Found: C, 51.57; H, 6.58; N, 16.90.

EXAMPLE 18

Dimethyl N-{5-[2-(2-Amino-4-hydroxy-5,6,7,8-tetrahydropyrido[2,3-d]-pyrimidin-6-yl)ethyl] pyrazol-3-ylcarbonyl}-L-glutamate From 5-[2-(amino-4-hydroxy-5,6,7,8-tetrahydropyrido[2, 3-d]pyrimidin-6-yl)ethyl]pyrazole-3-carboxylic acid (228 mg g, 0.75 mmol), 2-chloro-4,6-dimethoxy-1,3,5-triazine (145 mg, 0.825 mmol), 4-methylmorpholine (0.20 mL, 1.8 mmol), and dimethyl L-glutamate hydrochloride (191 mg, 0.9 mmol), there is obtained according to the procedure of Example 15, dimethyl N-{5-[2-(2-amino-4-hydroxy-5,6,7,8 -tetrahydropyrido[2,3-d]pyrimidin-6-yl)ethyl]pyrazol-3-ylcarbonyl}-L-glutamate (175 mg, 51%, mp 219–221° C.); $^1$H NMR (CDCl$_3$/CD$_3$OD, 3/1) δ 6.55 (s, 1H), 4.62 (m, 1H), 3.77 (s, 3H), 3.54 (s, 3H), 3.18 (brd, 1H, J=11.6 Hz), 2.79 (m, 1H), 2.61 (m, 2H), 2.43 (brd, 1H, J=15.0 Hz), 2.37 (t, 2H, J=4.3 Hz), 2.18 (m, 1H), 2.03 (m, 1H), 1.78 (dd, 1H, J=15.0 Hz), 1.63–1.35 (m, 3H). HR FAB MS calcd for C$_{20}$H$_{28}$N$_7$O$_6$ 462.2101 (M$^+$+H), found 462.2094.

EXAMPLE 19

N-{4-[2-(Amino-4-hydroxy-5,6,7,8-tetrahydropyrido [2,3-d]pyrimidin-6-yl)ethyl]pyrrol-2-ylcarbonyl}-L-glutamic Acid A solution of dimethyl N-{4-[2-(amino-4-hydroxy-5,6,7, 8-tetrahydropyrido-[2,3-d]pyrimidin-6-yl)ethyl]pyrrol-2-ylcarbonyl}-L-glutamate (92 mg, 0.2 mmol) in 1N sodium hydroxide (1 mL) was stirred at room temperature for 3 days, then acidified to pH 5 by addition of glacial acetic acid. The white solid was collected by filtration, washed with water, and dried in vacuo to give N-{4-[2-(amino-4-hydroxy-5,6,7,8-tetrahydropyrido[2,3-d]pyrimidin-6-yl) ethyl]pyrrol-2-ylcarbonyl}-L-glutamic acid (68 mg, 79%) as a white solid: $^1$H NMR (DMSO-d$_6$) δ 11.44 (s, 1H), 9.84 (br s, 1H), 7.79 (d, 1H, J=7.7 Hz), 6.64 (s, 2H), 6.23 (s, 1H), 5.97 (s, 2H), 4.27 (s, 1H), 3.16 (brd, 1H, J=9.6 Hz), 2.74 (brt, 1H, J=10.2 Hz), 2.45–2.18 (m, 5H), 1.95–1.75 (m, 3H), 1.65–1.40 (m, 3H). HR FAB MS calcd for C$_{19}$H$_{25}$N$_6$O$_6$ 433.1836 (M$^+$+H), found 433.1866.

Anal. Calcd for C$_{19}$H$_{24}$N$_6$O$_6$.1.5H$_2$O: C, 49.65; H, 5.93; N, 18.30. Found: C, 49.28; H, 5.89; N, 18.38.

EXAMPLE 20

N-{5-[2-(2-Amino-4-hydroxy-5,6,7,8-tetrahydropyrido [2,3-d]pyrimidin-6-yl)ethyl]pyrrol-2-ylcarbonyl}-L-glutamic Acid Similarly prepared from dimethyl N-{5-[2-(2-Amino-4-hydroxy-5,6,7,8-tetrahydropyrido[2,3-d]pyrimidin-6-yl) ethyl]pyrrol-2-yl[carbonyl]-L-glutamate (138 mg g, 0.3 mmol) and 1N sodium hydroxide (1.5 mL) according to the procedure of Example 19 is N-{5-[2-(2-amino-4-hydroxy-5,6,7,8-tetrahydropyrido[2,3-d]pyrimidin-6-yl)ethyl]pyrrol-2-ylcarbonyl}-L-glutamic acid as an off white solid (105 mg, 81%), mp >260° C.: $^1$H NMR (DMSO-d$_6$) δ 11.22 (s, 1H), 9.76 (br s, 1H), 7.83 (d, 1H, J=7.8 Hz), 6.69 (s, 1H), 6.27 (s, 1H), 5.97 (s, 2H), 5.81 (s, 1H), 4.32 (s, 1H), 3.16 (m, 1H), 2.73 (m, 1H), 2.61–2.24 (m, 3H), 2.28 (m, 2H), 2.02–1.69 (m, 3H), 1.60– 1.43 (m, 3H). HR FAB MS calcd for C$_{19}$H$_{25}$N$_6$O$_6$ 433.1836 (M$^+$+H), found 433.1840.

Anal. Calcd for C$_{19}$H$_{24}$N$_6$O$_6$.0.5 H$_2$O: C, 51.70; H, 5.71; N, 19.04. Found: C, 51.79; H, 5.90; N, 18.87.

EXAMPLE 21

N-{5-[2-(Amino-4-hydroxy-5,6,7,8-tetrahydropyrido [2,3-d]pyrimidin-6-yl)ethyl]pyrrol-3-ylcarbonyl}-L-glutamic Acid From dimethyl N-{5-[2-(amino-4-hydroxy-5,6,7,8-tetrahydropyrido[2,3-d]-pyrimidin-6-yl)ethyl]pyrrol-3-ylcarbonyl}-L-glutamate (92 mg g, 0.2 mmol) and 1N sodium hydroxide (1 mL), there is similarly obtained according to the procedure of Example 19 N-{5-[2-(amino-4-hydroxy-5,6,7,8-tetrahydropyrido[2,3-d]pyrimidin-6-yl) ethyl]pyrrol-3-ylcarbonyl}-L-glutamic acid as an off-white solid (57 mg, 66%, mp >260° C.): $^1$H NMR (CD$_3$OD) δ 7.25 (d, 1H, J=1.6 Hz), 6.30 (d, 1H, J=1.6 Hz), 4.53 (m, 1H), 3.33 (m, 1H), 2.92 (dd, 1H, J=12.2, 8.5 Hz), 2.70–2.60 (m, 3H), 2.43 (t, 2H, J=7.6 Hz), 2.22 (m, 1H), 2.08-1.96 (m, 2H), 1.76 (m, 1H), 1.66 (m, 2H). HR FAB MS calcd for C$_{19}$H$_{25}$N$_6$O$_6$ 433.1836(M$^+$+H), found 433.1858.

Anal. Calcd for C$_{19}$H$_{24}$N$_6$O$_6$.H$_2$O: C, 50.66; H, 5.82; N, 18.66. Found: C, 50.58; H, 5.58; N, 18.37.

EXAMPLE 22

N-{5-[2-(2-Amino-4-hydroxy-5,6,7,8-tetrahydropyrido[2,3-d]pyrimidin-6-yl)ethyl] pyrazol-3-ylcarbonyl}-L-glutamic Acid From dimethyl N-{ 5-[2-(2-amino-4-hydroxy-5,6,7,8-tetrahydropyrido[2,3-d]pyrimidin-6-yl)ethyl]pyrazol-3-ylcarbonyl}-L-glutamate (92 mg, 0.2 mmol) and 1N sodium hydroxide (0.5 mL), there is similarly obtained according to the procedure of Example 19, N-{ 5-[2-(2-amino-4-hydroxy-5,6,7,8-tetrahydropyrido[2,3-d]pyrimidin-6-yl) ethyl]-pyrazol-3-ylcarbonyl}-L-glutamic acid (69 mg, 79%, mp >260° C.): $^1$H NMR (DMSO-$d_6$) δ 12.90 (br s, 1H), 9.84 (br s, 1H), 7.99 (d, 1H, J=7.7 Hz), 6.43 (s, 1H), 6.26 (s, 1H), 5.98 (s, 2H), 4.24 (m, 1H), 3.16 (brd, 1H, J=10.4 Hz), 2.77 (m, 1H), 2.67 (m, 2H), 2.47 (brd, 1H, J=15.0 Hz), 2.26 (m, 2H), 2.05–1.74 (m, 3H), 1.68–1.45 (m, 3H). HR FAB MS calcd for $C_{18}H_{24}N_7O_6$ 434.1788 ($M^+$+H), found 434.1813.

EXAMPLE 23

Dimethyl N-{2-[2-(2-Pivaloylamino-4-hydroxypyrido[2,3-d]pyrimidin-6-yl)ethynyl]-1-triphenylmethylimidazol-4-ylcarbonyl}-L-glutamate Following the procedure of Example 1, dimethyl N-(2-iodo-1-triphenylmethylimidazol-4-ylcarbonyl)-L-glutamate (638 mg, 1.0 mmol), 2-pivaloylamino4-hydroxy-6-ethynylpyrido[2,3-d]pyrimidine (541 mg, 2.0 mmol), $Pd(PPh)_2Cl_2$ (35 mg, 0.05 mmol), cuprous iodide (19 mg, 0.1 mmol), triethylamine (0.7 mL), and acetonitrile (50 mL) yield dimethyl N-(2-[2-(2-pivaloylamino-4-hydroxypyrido[2,3-d]pyrimidin-6-yl)ethynyl]-1-triphenylmethylimidazol-4-ylcarbonyl}-L-glutamate [515 mg, 66% after flash column chromatography (ethyl acetate:hexanes, 2:1), mp 93–95° C]: $^1$H NMR (CDCl$_3$) δ 12.05 (br s, 1H), 8.43 (br s, 1H), 8.26 (s, 1H), 7.93 (d, 1H, J=2.2 Hz), 7.61 (s, 1H), 7.54 (d, 1H, J=7.6 Hz), 7.33–7.28 (m, 9H), 7.18–7.12 (m, 6H), 4.77 (m, 1H), 3.74 (s, 3H), 3.65 (s, 3H), 2.45 (m, 2H), 2.32 (m, 1H), 2.05 (m, 1H), 1.30 (s, 9H). HRMS calcd for $C_{44}H_{41}N_7O_7$ 779.3067, found 779.3088.

Anal. Calcd for $C_{44}H_{41}$ $N_7O_7$: C, 67.77; H, 5.30; N, 12.57. Found: C, 67.48; H, 5.59; N, 22.72.

The starting material can be prepared in the following manner. A mixture of 2-iodo-4-hydroxymethyl-1-(triphenylmethyl)imidazole (3.264 g, 7.0 mmol) and manganese dioxide (12.17 g, 140 mmol) in methylene chloride (100 mL) was stirred overnight at room temperature and filtered though Celite. The filtrate was concentrated in vacuo to give 2-iodo-4-formyl-1-triphenylmethylimidazole as a white foamy solid (3.05 g, 94%), mp 173–75° C. which was sufficiently pure to be used in the next step without further purification. $^1$H NMR (CDCl$_3$) δ 9.77 (s, 1H), 7.55 (s, 1H), 7.38–7.30 (m, 9H), 7.16–7.09 (m, 6H).

Anal. Calcd for $C_{23}H_{17}IN_2O$: C, 59.50; H, 3.69; N, 6.03. Found: C, 59.27; H, 3.76; N, 5.95.

To a mixture of activated manganese dioxide (5.66 g, 65 mmol), sodium cyanide (833 mg, 17 mmol), and glacial acetic acid (300 mg) in methanol (70 mL) was added 2-iodo-4-formyl-1-triphenylmethylimidazole (2.33 g, 5.0 mmol) in one portion. The mixture was stirred for 1 hour at room temperature and then filtered through Celite. The filtrate was concentrated and the residue was partitioned into methylene chloride and water. The organic phase was dried (magnesium sulfate) and concentrated in vacuo to give a white foamy solid. Purification by column chromatography using ethyl acetate:hexanes (1:2) afforded 2-iodo-4-(methoxycarbonyl)-1-triphenylmethylimidazole (2.26 g, 92%) as a white solid, mp 192–194° C. $^1$H NMR (CDCl$_3$) δ 7.55 (s, 1H), 7.37–7.29 (m, 9H), 7.18–7.09 (m, 6H), 3.84 (s, 3H).

Anal. Calcd for $C_{24}H_{19}IN_2O_2$: C, 58.31; H, 3.87; N, 5.67. Found: C, 58.03; H, 3.90; N, 5.64.

A suspension of 2-iodo-4-(methoxycarbonyl)-1-triphenylmethylimidazole (1.978 g, 4 mmol) in 6N sodium hydroxide (15 mL) was heated at reflux for 4 hours. The resulting suspension was diluted with ethyl acetate (20 mL) and then slightly acidified with acetic acid. The resulting clear solution was extracted three times with ethyl acetate (20 mL) and the combined extracts were dried (magnesium sulfate) and concentrated in vacuo. Residual acetic acid was removed under high vacuum to give 2-iodo-1-triphenylmethylimidazole-4-carboxylic acid (1.67 g, 87%) as a white solid, mp 203–205° C.: $^1$H NMR (CDCl$_3$) δ 7.60 (s, 1H), 7.38–7.20 (m, 9H), 7.18–7.09 (m, 6H).

Anal. Calcd for $C_{23}H$ 17I$N_2O_2$: C, 57.52; H, 3.57; N, 5.83. Found: C, 57.37; H, 3.87; N, 5.65.

2-Iodo-1-triphenylmethylimidazole-4-carboxylic acid (1.443 g, 3.0 mmol), 2-chloro-4,6-dimethoxy-1,3,5-triazine (553 mg, 3.15 mmol), 4-methylmorpholine (0.614 mL, 6.6 mmol), dimethyl L-glutamate hydrochloride (698 mg, 3.3 mmol), and tetrahydrofuran (20 mL) were then allowed to react in the manner described in Example 15 to yield dimethyl N-(2-iodo-1-triphenylmethylimidazol-4-ylcarbonyl)--L-glutamate (1.44 g, 75%, mp 86–88° C.): $^1$H N (CDCl$_3$) δ 7.47 (s, 1H), 7.44 (d, 1H, J=8.6 Hz), 7.32–7.26 (m, 9H), 7.21–7.05 (m, 6H), 4.72 (m, 1H), 3.71 (s, 3H), 3.62 (s, 3H), 2.41 (m, 2H), 2.27 (m, 1H), 1,99 (m, 1H). HRMS calcd for $C_{30}H_{28}IN_3O_5$ 637.1074, found 637.1054. Anal. Calcd for $C_{30}H_{28}IN_3O_5$: C, 56.52; H, 4.43; N, 6.59. Found: C, 56.36; H, 4.45, N, 6.57.

EXAMPLE 24

Dimethyl N-{2-[2-(2-Pivaloylamino-4-hydroxy-5,6,7,8-tetrahydropyrido[2,3-d]pyrimidin-6-yl)ethyl]imidazol-4-ylcarbonyl}-L-glutamate A mixture of dimethyl N-{2-[2-(2-pivaloylamino-4-hydroxypyrido[2,3-d]-pyrimidin-6-yl)ethynyl]-1-triphenylmethylimidazol-4-ylcarbonyl}-L-glutamate (390 mg, 0.5 mmol) and 10% palladium-on-carbon catalyst (390 mg) in methanol (15 mL) was stirred under 50 psi of hydrogen for 7 days at room temperature. The workup was performed as described in Example 2 to yield 130 mg (48%) of dimethyl N-{2-[2-(2-pivaloylamino-4-hydroxy-5,6,7,8-tetrahydropyrido[2,3-d]pyrimidin-6-yl)ethyl]imidazol-4-ylcarbonyl}-L-glutamate as a pale yellow solid, mp 129–131° C.: $^1$H NMR (CDCl$_3$) δ 11.35 (br s, 1H), 8.95 (br s, 1H), 7.54 (d, 1H, J=8.4 Hz), 7.49 (s, 1H), 4.75 (m, 1H), 3.69 (s, 3H), 3.60 (s, 3H), 3.30 (M, 1H), 2.87 (m, 1H), 2.80–2.60 (m, 3H), 2.43 (m, 2H), 2.27 (m, 1H), 2.15–1.92 (m, 2H), 1.80–1.60 (m, 3H), 1.26 (s, 9H).

EXAMPLE 25

N-{2-[2-(Amino-4-hydroxy-5,6,7,8-tetrahydropyrido[2,3d]pyrimidin-6-yl)ethyl]imidazol-4-ylcarbonyl}-L-glutamic Acid Dimethyl N-{2-[2-(2-pivaloylamino-4-hydroxy-5,6,7,8-tetrahydropyrido[2,3-d]-pyrimidin-6-yl)ethyl]imidazol-4-ylcarbonyl}-L-glutamate (109 mg g, 0.2 mmol) and 0.5N sodium hydroxide (1 mL) are allowed to react analogously to the method described in Example 19 to yield N-{2-[2-(amino-4-hydroxy-5,6,7,8-tetrahydropyrido-[2,3-d]pyrimidin-6-yl)ethyl]imidazol-4-ylcarbonyl}-L-glutamic acid (38 mg, 44%, mp >260° C.): $^1$H NMR (DMSO$d_6$) d 12.35 (br s, 1H), 12.21 (br s, 1H), 9.77 (br s, 1H), 7.80 (br s, 1H), 7.50 (s, 1H), 6.27 (s, 1H), 5.92 (s, 2H), 4.37 (m, 1H), 3.17 (br d, 1H, J=10.6 Hz), 2.79–2.61 (m, 3H), 2.44 (m, 1H), 2.26 (m, 2H), 2.07–1.76 (m, 3 H), 1.68–1.59 (m, 3H).

EXAMPLE 26

Diethyl N-{2-[2-Pivaloylamino-4-hydroxypyrido[2,3-d]pyrimidin-6-ylethynyl]-4-thiazolylcarbonyl}-L-glutamate To a 100 mL 14/20 round bottom flask under an argon atmosphere were added 0.316 g (1.17 mmol) of 2-pivaloylamino-4-hydroxy-6-ethynylpyrido[2,3-d]pyrimidine suspended in 10 mL of acetonitrile, followed by the addition of 0.47 g (1.2 mmol) of diethyl N-(2-bromo-4-thiazolylcarbonyl)-L-glutamate, 0.14 g (0.12 mmol) of tetrakis(triphenylphosphine)palladium (0), 0.046 g (0.24 mmol) of copper (I) iodide, and 0.35 mL (2.5 mmol) of triethylamine with an additional 10 mL of acetonitrile. The reaction was heated to reflux for 2 hours The volatiles were removed in vacuo, and the residue purified using silica gel flash chromatography, eluting with a step gradient of 100% chloroform to 2% methanol/chloroform to give 0.46 g (67%) of diethyl N-{2-[2-pivaloylamino-4-hydroxypyrido[2,3-d]pyrimidin-6-ylethynyl]-4-thiazolylcarbonyl}-L-glutamate as an off-white solid, m.p. 201–202° C. (dec). $R_f$=0.28 (4% methanol/chloroform). 1H NMR (300 MHz, DMSO-$d_6$) δ 1.12–1.29 (m, 15H), 2.05– 2.15 (m, 1H), 2.37 (t, J=7.2 Hz, 2H), 3.98–4.13 (m, 4H), 4.45–4.49 (m, 1H), 8.47 (s, 1H), 8.61 (d, J=1.8 Hz, 1H), 8.84 (d, J=8.1 Hz, 1H), 9.07 (d, J=1.9 Hz, 1H)

The starting material can be prepared as follows.

To a 100 mL 24/40 round bottom flask was charged 3.25 g (13.8 mmol) of 2-bromo-4-thiazolecarboxylic acid ethyl ester (Helv. Chim. Acta, 1942, 25, 1073) dissolved in 20 mL of 1N sodium hydroxide. The reaction was stirred at room temperature for 3 h, cooled down in an ice bath and acidified to pH 2 with 5N hydrochloric acid. The white precipitate was filtered, washed with 20 mL cold water, and dried in a vacuum oven to give 2.7 g (94%) of 2-bromo-4-thiazolecarboxylic acid. m.p. 227–229° C., $R^f$=0.16 (20% methanol/chloroform). 1H NMR (300 MHz, DMSO-$d_6$) δ 8.43 (s, 1H).

Anal. Cal'd for $C_4H_2BrNO_3S$: C, 23.10; H, 0.97; N, 6.73. Found: C, 23.42; H, 0.97; N, 6.51.

To a 100 mL 14/20 round bottom flask under a nitrogen atmosphere was charged 1.7 g (8.17 mmmol) of 2-bromo-4-thiazolecarboxylic acid in 17 mL of benzene, followed by the addition of 2.4 mL (33 mmol) of thionyl chloride, and a catalytic amount of dimethylformamide. The reaction was heated to reflux for 2 hours The volatiles were removed in vacuo, and this residue was then dissolved in 20 mL of methylene chloride and added dropwise to an ice-bath cooled mixture of 2.06 g (8.58 mmol) of L-glutamic acid diethyl ester, 2.39 mL (10.1 mmol) of triethylamine, and 10 mg of dimethylaminopyridine in 30 mL of methylene chloride. After the addition, the ice bath was removed and the reaction was stirred at room temperature for 2 hours The reaction was diluted with methylene chloride, washed with 0.5 N hydrochloric acid, water, 5% sodium bicarbonate, water, dried over sodium sulfate, and removed in vacuo. The crude residue was purified using silica gel flash chromatography eluting with 3:1 chloroform/ether to give 2.7 g (84%) of diethyl N-(2-bromo-4-thiazolylcarbonyl)-L-glutamate as a yellow oil. $R_f$=0.43 (3:1 chloroform/ether). 1H NMR (300 MHz, DMSO-$d_6$) δ 1.14 (q, J=7.1 Hz, 6H), 1.98–2.18 (m, 2H), 2.35 (t, J=7.3 Hz, 2H), 3.97–4.11 (m, 4H), 4.37–4.50 (m, 1H), 8.28 (d, J=5.9 Hz, 1H), 8.73 (d, J=7.7 Hz, 1H)

Anal. Cal'd for $C_{13}H_{17}BrN_2O_5S$: C, 39.71; H, 4.36; N, 7.12. Found: C, 39.84; H, 4.29; N, 7.36.

EXAMPLE 27

Diethyl N-{2-[2-(2-Pivaloylamino-4-hydroxy-5,6,7,8-tetrahydropyrido[2,3-d]pyrimidin-6-yl)ethyl]-4-thiazolylcarbonyl}-L-glutamate To a 50 mL round bottom flask were charged 0.25 g (0.43 mmol) of diethyl N-{2-[2-pivaloylamino4-hydroxypyrido[2,3-d]pyrimidin-6-ylethynyl]-4-thiazolylcarbonyl}-L-glutamate dissolved in 8 mL of glacial acetic acid, followed by the addition of 0.25 g of platinum oxide catalyst. The reaction was then stirred under hydrogen at 1 atmosphere for 24 hours The catalyst was then filtered away, and the filtrate was removed in vacuo. The residue was then purified using silica gel flash chromatography eluting with 2% methanol/chloroform to give 0.092 g (36%) of diethyl N-{2-[2-(2-pivaloylamino-4-hydroxy-5,6,7,8-tetrahydropyrido[2,3-d]pyrimidin-6-yl)ethyl]-4-thiazolylcarbonyl}-L-glutamate, m.p. 63–166° C., as a yellow solid. $R_f$=0.28 (5% methanol/chloroform); 1H NMR (300 MHz, DMSO $d_6$) δ 1.09–1.23 (m, 15H), 1.73–1.77 (m, 3H), 1.97–2.10 (m, 4H), 2.34 (t, J=7.2 Hz, 2H), 2.50–2.62 (m, 2H), 2.86-2.95 (m, 1H), 3.08–3.12 (m, 2H), 3.964.11 (m, 4H), 4.43–4.45 (m, 1H), 6.46 (s, 1H), 8.14 (s, 1H), 8.48 (d, J=8.0 Hz, 1H).

EXAMPLE 28

N-{2-[2-(2-Amino-4-hydroxy-5,6,7,8-tetrahydropyrido[2,3-d]pyrimidin-6-yl)ethyl]-4-thiazolylcarbonyl}-L-glutamic Acid To a 25 mL 14/20 round bottom flask was charged 0.067 g (0.11 mmol) of diethyl N-{2-[2-(2-pivaloylamino-4-hydroxy-5,6,7,8-tetrahydropyrido[2,3-d]pyrimidin-6-yl)ethyl]-4-thiazolylcarbonyl}-L-glutamate dissolved in 3 mL of 1N sodium hydroxide. The reaction was stirred at room temperature for 84 hours The solution was cooled down in an ice bath and acidified with 1N hydrochloric acid to pH 3. The precipitate was filtered, washed with 25 mL water, and dried in a vacuum oven at 60° C. to give 0.036 g (70%) of N-{2-[2-(2-amino-4-hydroxy-5,6,7,8-tetrahydropyrido[2,3-d]pyrimidin-6-yl)ethyl]-4-thiazolylcarbonyl}-L-glutamic acid m.p. 210–212° C. as a tan solid. $R_f$=0.08 (50% methanol/chloroform); 1H NMR (300 MHz, DMSO $d_6$) δ 1.69–2.09 (m, 8H), 2.26 (t, J=7.1 Hz, 2H), 2.80 (t, J=8.2 Hz, 2H), 3.05–3.17 (m, 2H), 4.34–4.41 (m, 1H), 5.93 (s, 2H), 6.26 (s, 1H), 8.12 (s, 1H), 8.33 (d, J=7.7 Hz, 1H), 9.70 (br s, 1H).

EXAMPLE 29

Diethyl N-{2-[2-Pivaloylamino-4-hydroxypyrido[2,3-d]pyrimidin-6-yl-ethynyl]-5-thiazolylcarbonyl}-L-glutamate In a similar fashion to that described in Example 26, there is obtained from 2-pivaloylamino-4-hydroxy-6-ethynylpyrido[2,3-d]pyrimidine (0.57 mmol) and of N-(2-bromo-5-thiazolylcarbonyl)-L-glutamic acid diethyl ester (0.58 mmol), 0.19 g (56%) of diethyl N-{2-[2-pivaloylamino-4-hydroxypyrido[2,3-d]pyrimidin-6-ylethynyl]-5-thiazolylcarbonyl}-L-glutamate as an off-white solid m.p. 223–225° C. (dec). $R_f$=0.25 (5% methanol/chloroform). 1H NMR (300 MHz, DMSO $d_6$) δ 1.17 (q, J=7.5 Hz, 6H), 1.25 (s, 1H), 1.95–2.11 (m, 2H), 2.42–2.48 (m, 2H), 3.99–4.14 (m, 4H), 4.38445 (m, 1H), 8.29 (s, 1H), 8.63 (d, J=2.1 Hz, 1H), 9.08 (d, J=2.0 Hz, 1H), 9.12 (d, J=7.4 Hz, 1H).

Anal. Cal'd for $C_{27}H_{30}N_6O_6S$: C, 55.66; H, 5.19; N, 14.42. Found: C, 55.95; H, 5.16; N, 14.57.

The starting material can be prepared as follows: To a 500 mL 24/40 3-neck round bottom flask equiped with a mechanical stirrer, was charged 3.4 g (19.7 mmol) of 2-amino-5-thiazolecarboxylic acid ethyl ester (Ber., 1888, 21, 938), partially dissolved in 30 mL of concentrated phosphoric acid. The stirring mixture was cooled in an ice bath and then 9 mL of concentrated nitric acid was added slowly, followed by the dropwise addition of 2.85 g (41.3 mmol) of sodium nitrite in 5 mL of water. The mixture was stirred in the cold for 35 minutes, and then added dropwise was 3.0 g (47.2 mmol) of copper powder in 75 mL of 48% hydrobromic acid cooled to −10° C. After the evolution of nitrogen gas ceased, the thick reaction mixture was removed from the ice bath and neutralized to pH 8, first using 5N sodium hydroxide and then sodium carbonate. The aqueous was then extracted with 400 mL ether. The insoluble material was filtered away and the filtrate was washed with 5% sodium bicarbonate, water, dried over sodium sulfate, and removed in vacuo. The crude residue was then purified using silica gel flash chromatography eluting with 1:1 ether/hexanes to give 2.4 g (52%) of 2-bromo-5-thiazolecarboxylic acid ethyl ester as a yellow oil. $R_f$=0.62 (1:1 ether/hexanes). 1H NMR (300 MHz, DMSO $d_6$) δ 1.26 (t, J=7.0 Hz, 3H), 4.29 (q, J=7.1 Hz, 2H), 8.28 (s, 1H).

Anal. Cal'd for $C_6H_6BrNO_2S$: C, 30.53; H, 2.56; N, 5.93. Found: C, 30.78; H, 2.62; N, 5.98.

To a 100 mL 14/20 round bottom flask was charged 2.4 g (10.1 mmol) of 2-bromo-5-thiazolecarboxylic acid ethyl ester dissolved in 14 mL of 1N sodium hydroxide. The reaction was stirred at room temperature for 1.5 hours The yellow solution was acidified with 5N hydrochloric acid to pH 2. The solid which formed was cooled in an ice bath, filtered, washed with water, and dried in a vacuum oven at 60° C. to give 1.9 g (90%) of 2-bromo-5-thiazolecarboxylic acid m.p. 185–186° C. (dec) as a white solid. $R_f$=0.12 (20% methanol/chloroform). 1H NMR (300 MHz, DMSO $d_6$) δ 8.19(s, 1H).

To a 100 mL 14/20 round bottom flask under a nitrogen atmosphere was charged 1.0 g (4.81 mmmol) of 2-bromo-4-thiazolecarboxylic acid in 10 mL of benzene, followed by the addition of 1.4 mL (19 mmol) of thionyl chloride, and a catalytic amount of dimethylformamide. The reaction was heated to reflux for 2 hours The volatiles were removed in vacuo, and this residue was then dissolved in 15 mL of methylene chloride and added dropwise to an ice-bath cooled mixture of 1.21 g (5.05 mmol) of L-glutamic acid diethyl ester, 1.41 mL (10.1 mmol) of triethylamine, and 5 mg of dimethylaminopyridine in 15 mL methylene chloride. After the addition, the ice bath was removed and the reaction was stirred at room temperature for 2 hours The reaction was diluted with methylene chloride, washed with 0.1 N hydrochloric acid, water, 5% sodium bicarbonate, water, dried over sodium sulfate, and removed in vacuo. The crude residue was purified using silica gel flash chromatography eluting with a gradient of 1:2 ethyl acetate/hexanes to 1:1 ethyl acetate/hexanes to give 0.9 g (48%) of N-[(2-bromo-5-thiazolyl)carbonyl]-L-glutamic acid diethyl ester as a yellow oil. $R_f$=0.30 (1:2 ethyl acetate/hexanes), 1H NMR (300 MHz, $CDCl_3$) δ 1.24–1.34 (m, 6H), 2.15–2.32 (m, 2H), 2.47–2.55 (m, 2H), 4.12–4.30 (m, 4H), 4.64–4.71 (m, 1H), 7.97 (s, 1H).

EXAMPLE 30

Diethyl N-{2-[2-(2-Pivaloylamino-4-hydroxy-5,6,7,8-tetrahydropyrido-[2,3-d]pyrimidin-6-yl)ethyl]-5-thiazolylcarbonyl}-L-glutamate In a similar fashion to that described in Example 27, there is obtained from diethyl N-{2-[2-pivaloylamino-4-hydroxypyrido[2,3-d]pyrimidin-6-ylethynyl]-5-thiazolylcarbonyl}-L-glutamate, diethyl N-{2-[2-(2-pivaloylamino-4-hydroxy-5,6,7,8-tetrahydropyrido[2,3-d] pyrimidin-6-yl)ethyl]-5-thiazolylcarbonyl}-L-glutamate as a yellow solid, m.p. 156–159° C.; $R_f$=0.36 (10% methanol/chloroform); 1H NMR (300 MHz, DMSO-$d_6$) δ 1.11–1.23 (m, 15H), 1.66–1.76 (m, 3H), 1.89–2.08 (m, 3H), 2.40 (t, J=7.4 Hz, 2H), 2.51–2.55 (m, 1H), 2.85–2.89 (m, 1H), 3.06 (t, J=6.6 Hz, 1H), 3.14 (d, J=5.2 Hz, 2H), 3.98–4.11 (m, 4H), 4.33–4.37 (m, 1H), 6.45 (s, 1H), 8.30 (s, 1H), 8.84 (d, J=7.4 Hz, 1H).

EXAMPLE 31

N-{2-[2-(2-Amino-4-hydroxy-5,6,7,8-tetrahydropyrido[2,3-d]pyrimidin-6-yl)ethyl]-5-thiazolylcarbonyl}-L-glutamic Acid In a similar fashion to that described in Example 28, there is obtained from diethyl N-{2-[2-(2-pivaloylamino-4-hydroxy-5,6,7,8-tetrahydropyrido[2,3-d]pyrimidin-6-yl) ethyl]-5-thiazolylcarbonyl}-L-glutamate, N-{2-[2-(2-amino-4-hydroxy-5,6,7,8-tetrahydropyrido[2,3-d] pyrimidin-6-yl)ethyl]-5-thiazolylcarbonyl}-L-glutamic acid, as a pale yellow solid, m.p. 197–199° C. (dec); $R_f$=0.09 (50% methanol/chloroform); 1H NMR (300 MHz, DMSO $d_6$) δ 1.67–1.92 (m, 6H), 2.03–2.08 (m, 2H), 2.33 (t, J=7.0 Hz, 2H), 2.79–2.82 (m, 1H), 3.10–3.21 (m, 2H), 4.33–4.40 (m, 1H), 5.95 (s, 2H), 6.28 (s, 1H), 8.31 (s, 1H), 8.75 (d, J=7.7 Hz, 1H), 9.75 (br s, 1H)

EXAMPLE 32

Hard gelatin capsules are prepared using the following ingredients:

|  | Quantity (mg/capsule) |
| --- | --- |
| N-{3-[2-(2-amino-4-hydroxy-5,6,7,8-tetrahydropyrido 2,3-d]pyrimidin-6-yl)ethyl]-pyrazol-5-ylcarbonyl}-L-glutamic acid | 250 |
| Starch, dried | 200 |
| Magnesium stearate | 10 |
|  | 460 mg |

EXAMPLE 33

Tablets are prepared using the ingredients below:

|  | Quantity (mg/capsule) |
| --- | --- |
| N-{2-[2-(amino-4-hydroxy-5,6,7,8-tetrahydropyrido-[2,3-d]pyrimidin-6-yl)ethyl]-imidazol-4-ylcarbonyl}-L-glutamic acid | 250 |
| Cellulose, microcrystalline | 400 |
| Silicon dioxide, fumed | 10 |
| Stearic acid | 5 |
|  | 665 mg |

The components are blended and compressed to form tablets each weighing 665 mg.

EXAMPLE 34

An intravenous formulation may be prepared as follows:

|  | Quantity |
|---|---|
| N-{4-[2-(amino-4-hydroxy-5,6,7,8-tetrahydropyrido[2,3-d]-pyrimidin-6-yl)ethyl]pyrrol-2-ylcarbonyl}-L-glutamic acid | 100 mg |
| Isotonic saline | 1,000 mL |

The following examples illustrate specific aspects of the present invention and are not intended to limit the scope thereof in any respect and should not be so construed.

What is claimed is:

1. A compound selected from the group consisting of
   (i) a fused pyrimidine of the formula:

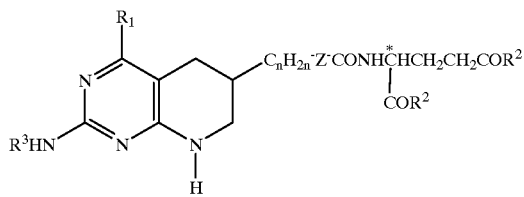

in which $R^1$ is —OH or —NH$_2$,
$R^2$ is —OH or an a carboxylic acid protecting group,
$R^3$ is —H or an amino protecting group,
Z is a divalent, five-membered, nitrogen-containing heterocyclic ring system optionally containing a sulfur or nitrogen atom as a second hetero ring member, said valence bonds originating from nonadjacent carbon atoms of said ring,
n has a value of 2 or 3, and
the configuration about the carbon atom designated * is L, and (ii) a pharmaceutically acceptable salt thereof.

2. A compound according to claim 1 in which Z is pyrrolediyl.

3. A compound according to claim 1 in which Z is imidazolediyl.

4. A compound according to claim 1 in which Z is pyrazolediyl.

5. A compound according to claim 1 in which Z is thiazolediyl.

6. A compound according to claim 1 in which $R^1$ is —OH, $R^2$ is —OH, $R^3$ is —H, and n has a value of 2.

7. A compound according to claim 6 in which said pyrimidine is N-{2-[2-(2-amino-4-hydroxy-5,6,7,8-tetrahydropyrido[2,3-d]pyrimidin-6-yl)ethyl]-pyrrol-5-ylcarbonyl}-L-glutamic acid.

8. A compound according to claim 6 in which said pyrimidine is N-{2-[2-(2-amino-4-hydroxy-5,6,7,8-tetrahydropyrido[2,3-d]pyrimidin-6-yl)ethyl]-pyrrol-4-ylcarbonyl}-L-glutamic acid.

9. A compound according to claim 6 in which said pyrimidine is N-{4-[2-(2-amino-4-hydroxy-5,6,7,8-tetrahydropyrido[2,3-d]pyrimidin-6-yl)ethyl]-pyrrol-2-ylcarbonyl}-L-glutamic acid.

10. A compound according to claim 6 in which said pyrimidine is N-{3-[2-(2-amino-4-hydroxy-5,6,7,8-tetrahydropyrido[2,3-d]pyrimidin-6-yl)ethyl]-pyrazol-5-ylcarbonyl}-L-glutamic acid.

11. A compound according to claim 6 in which said pyrimidine is N-{2-[2-(2-amino-4-hydroxy-5,6,7,8-tetrahydropyrido[2,3-d]pyrimidin-6-yl)ethyl]-thiazol-4-ylcarbonyl}-L-glutamic acid.

12. A compound according to claim 6 in which said pyrimidine is N-{2-[2-(2-amino-4-hydroxy-5,6,7,8-tetrahydropyrido[2,3-d]pyrimidin-6-yl)ethyl]-thiazol-5-ylcarbonyl}-L-glutamic acid.

13. A compound according to claim 6 in which said pyrimidine is N-{2-[2-(2-amino-4-hydroxy-5,6,7,8-tetrahydropyrido[2,3-d]pyrimidin-6-yl)ethyl]-imidazol-4-ylcarbonyl}-L-glutamic acid.

14. The method of inhibiting neoplastic growth in a mammal which growth is dependent on folic acid or a metabolic derivative of folic acid as a substrate, which comprises administering to the mammal in a single or multiple dose regimen an effective amount of a compound according to claim 1.

15. A pharmaceutical composition for inhibiting neoplastic growth in a mammal which growth is dependent on folic acid or a metabolic derivative of folic acid as a substrate, which comprises an amount of a compound according to claim 1 which upon administration to the mammal in a single or multiple does regimen is effective to inhibit said growth, in combination with a pharmaceutically acceptable carrier.

* * * * *